United States Patent [19]

Haines

[11] Patent Number: 4,977,903
[45] Date of Patent: Dec. 18, 1990

[54] SENSORY TRANSMITTING MEMBRANE DEVICE

[75] Inventor: Bernard M. Haines, Glenwood Springs, Colo.

[73] Assignee: Jerome F. Schweich, San Francisco, Calif.

[21] Appl. No.: 509,258

[22] Filed: Apr. 13, 1990

Related U.S. Application Data

[63] Continuation-in-part of Ser. No. 409,402, Sep. 19, 1989, abandoned.

[51] Int. Cl.$^5$ ............................ A61F 6/02; A61F 6/04
[52] U.S. Cl. .................................... 128/842; 128/844; 128/918
[58] Field of Search ................ 128/842, 844, 79, 918; 604/347-353, 330; 2/21

[56] References Cited

U.S. PATENT DOCUMENTS

| | | |
|---|---|---|
| D. 246,118 | 10/1977 | Okamoto . |
| D. 246,119 | 10/1977 | Okamoto . |
| 2,285,981 | 6/1942 | Johns ........................................ 2/21 |
| 2,379,624 | 7/1945 | Chisnell ................................... 2/21 |
| 2,586,674 | 2/1952 | Lönne . |
| 2,966,691 | 1/1961 | Cameron . |
| 3,809,090 | 5/1974 | Povlacs . |
| 4,829,991 | 5/1989 | Boeck ..................................... 128/79 |
| 4,852,586 | 8/1989 | Haines ................................. 128/842 |
| 4,919,149 | 4/1990 | Stang . |

Primary Examiner—Robert A. Hafer
Assistant Examiner—Michael Brown
Attorney, Agent, or Firm—Townsend and Townsend

[57] ABSTRACT

A sensory transmitting membrane device having a flexible base material including a plurality of solid or hollow projections integrally connected thereto and extending from opposite sides of the membrane. The projections on one side of the membrane are offset from the projections on the opposite side of the membrane and are positioned so that an edge of the base of a projection on one side of the membrane is in proximity to the opposite edge of the base of a projection on the other side of the membrane, whereby a linear motion of one projection in a direction parallel to the membrane results in a similar motion by any cooperating projections, to thereby enhance the transmission of tactile sensations from one side of the membrane material to the other side. The sensory transmitting device is particularly useful in latex or rubber surgical gloves, finger cots or condoms.

16 Claims, 2 Drawing Sheets

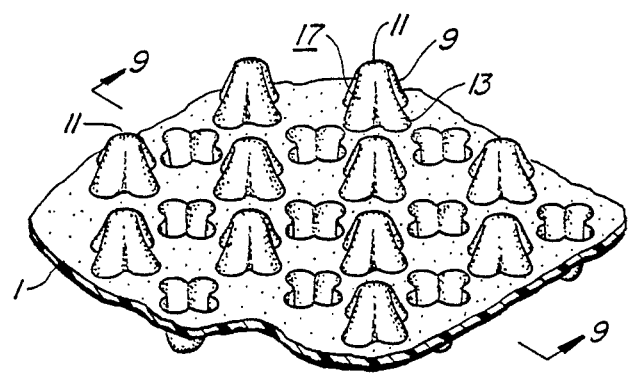
FIG._8.
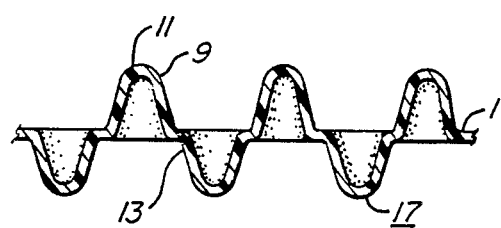
FIG._9.

SENSORY TRANSMITTING MEMBRANE DEVICE

This application is a continuation-in-part of pending application U.S. Ser. No. 07/409,402 in the name of Bernard M. Haines, filed Sept. 19, 1989, for Sensory Transmitting Membrane Device, now abandoned.

BACKGROUND OF THE INVENTION

The sensory transmitting membrane device of the present invention is an improvement on the sensory transmitting membrane device disclosed in my U.S. Pat. No. 4,852,586 dated Aug. 1, 1989, wherein an elastomeric base material is provided with a plurality of projection pairs, spaced apart and integrally formed with the base material, with each projection pair comprising two continuous coaxial projections extending from opposite sides of the base, whereby the transmission of acute tactile sensations from one side of the base material to the other is enhanced.

In the continuing research and experimentation of my sensory transmitting membrane device, it has been found that the transmission of tactile sensations from one side of the base material or membrane to the other can be further enhanced by offsetting the projections extending from opposite sides of the membrane. By this construction and arrangement, the projections extending from opposite sides of the membrane are positioned so that an edge of the base of a projection on one side of the membrane is in proximity to the opposite edge of the base of a projection on the other side of the membrane, whereby a linear motion of one projection in a direction parallel to the membrane results in a similar motion by any cooperating projections.

The above research and experimentation has also lead to the discovery that certain advantages can be obtained if the projections are hollow. The main advantage of hollow projections is that the manufacturing process is greatly simplified. In addition, the product is softer, which allows it to be rolled more easily and packed more compactly. If the membrane device is injection molded, the cycle time is reduced because the thinner parts heat and cool more rapidly. If a dipping process is used to manufacture the device, it can be formed by dipping a one piece mandrel into liquid elastomer and then removing the finished product by either stripping or air injection.

BRIEF DESCRIPTION OF THE DRAWINGS

FIG. 8 is a fragmentary, perspective view of the sensory transmitting device of the present invention in which the projections are hollow; and FIG. 9 is a view taken along line 9—9 in FIG. 8.

DETAILED DESCRIPTION OF THE DRAWINGS

Figure 1:
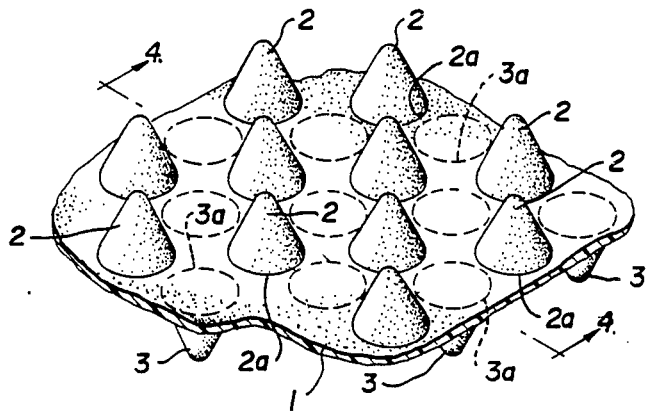
FIG. 1 is a fragmentary, perspective view of the sensory transmitting membrane device of the present invention in which the projections are solid.

Referring to the drawings and more particularly to FIG. 1, the sensory transmitting membrane device of the present invention comprises a flexible base or membrane 1 having a plurality of conical projections 2 and 3 integrally connected to and extending from opposite sides of the membrane 1. The device is preferably formed of a single, homogenous prophylactically impervious elastomeric material.

While each pair of projections in the device disclosed in my aforementioned U.S. Pat. No. 4,852,586 included two continuous coaxial projections extending from opposite sides of the base, the projections 2 and 3 in the device of the present invention, as seen in FIG. 4, are not continuous and coaxial but rather separate and offset from each other, whereby an edge 2a of the base of projection 2 is in proximity to the opposite edge 3a of the base of projection 3.

Figure 5:
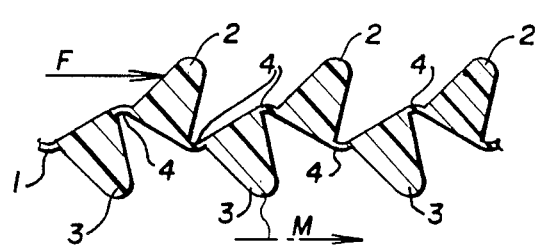
FIG. 5 is a sectional view similar to FIG. 4 illustrating the movement of the projections during the transmission of tactile sensations from one side of the membrane to the other.

FIG. 5 illustrates the responsive movement and direction of the projections 2 and 3 when a horizontal force F is applied to one projection 2. The projections 2 and 3 function as levers pivotally connected to each other by the membrane 1, as at 4, resulting in all the projections moving in the same direction M.

Figure 4:
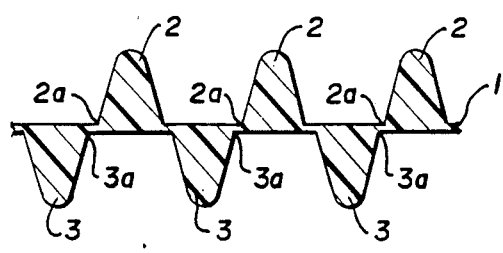
FIG. 4 is a view taken along line 4—4 of FIG. 1.
Figure 6:
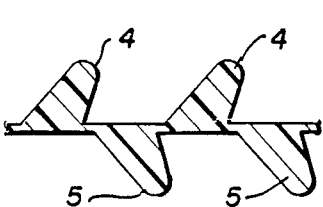
FIG. 6 is a fragmentary, sectional view of the device of the present invention showing another embodiment wherein the oppositely extending projections are inclined relative to the membrane.
Figure 7:
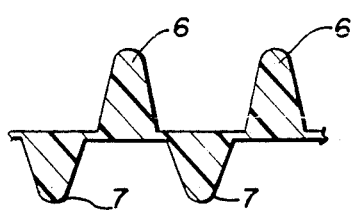
FIG. 7 is a fragmentary, sectional view of the device of the present invention illustrating yet another embodiment, wherein the projections extending from one side of the membrane are longer than those extending from the opposite side of the membrane.

While the projections 2 and 3 illustrated in FIGS. 1, 4 and 5 are of the same size and extend vertically from opposite sides of the membrane 1, FIG. 6 illustrates another embodiment wherein the projections 4 and 5 are of the same size but extend at an angle or are inclined relative to the membrane 1, and in FIG. 7 the projections 6 are longer than the oppositely extending projections 7.

Figure 2:
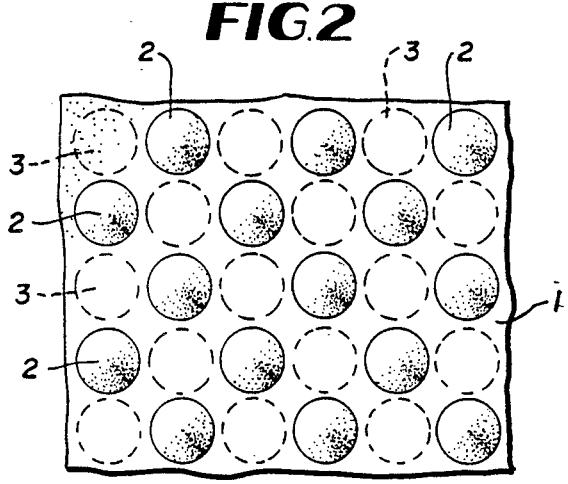
FIG. 2 is a top plan view of the device shown in FIG. 1.

As will be seen in FIGS. 1 and 2, the projections 2 and 3 are arranged in a rectangular array of rows and columns wherein in each row and column the projections 2 are spaced from each other with the projections 3 on the opposite side being spaced from each other and offset from the projections 2.

Figure 3:
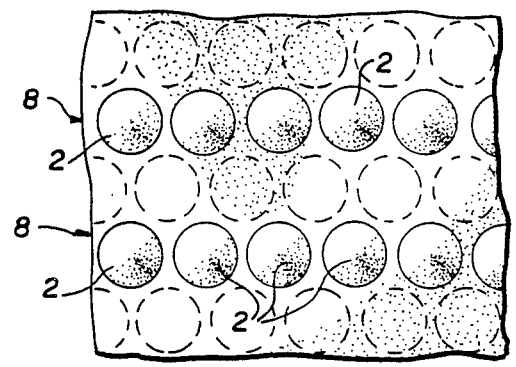
FIG. 3 is a top plan view of the device of the present invention showing another array of the oppositely extending projections.

In FIG. 3, the projections are arranged in a directional array wherein in each row 8 of projections 2, each projection is adjacent to the next projection with the rows of projections being spaced from each other. On the opposite side of the membrane, the projections 3 are similarly arranged and offset from the projections 2.

By offsetting the projections 2 and 3, the transmission of tactile sensations from one side of the membrane 1 to the other is enhanced particularly for use in latex or rubber surgical gloves, finger cots or condoms.

FIGS. 8 and 9 illustrate the device of the present invention with a plurality of hollow projections 9 extending from opposite sides of the membrane 1. Each projection 9 is terminated by a spherical cross-section 11 and has four lobes 13. Each projection 9 is, in the preferred embodiment, smooth over its surface. However, projections 9 could be provided with raised rings or other surface discontinuities on its outer surface 17 so that motion on the opposite side of the membrane can be more readily detected when lubricated. The embodiment of FIGS. 1-7 could be made with hollow, as opposed to solid, projections as well.

It is to be understood that the form of the invention herewith shown and described is to be taken as a preferred example of the same, and that various changes in the shape, size and arrangement of parts may be resorted to, without departing from the spirit of the invention or scope of the subjoined claims.

What is claimed is:

1. A device for the transmission of information between surfaces comprising a substantially homogenous elastomeric material base membrane having first and second sides and a plurality of first and second projections spaced apart and integrally formed with said base membrane, the first projections extending from the first side and the second projections extending from the second side 180° from the first projections, the projections being positioned so that an edge of the base of a first projection is in proximity to the opposite edge of the base of a second projection, whereby a force imparting a linear motion to a first projection in a direction parallel to the base membrane results in a similar motion by any cooperating second projections.

2. A device according to claim 1, wherein said information is tactile sensation.

3. A device according to claim 1, wherein said homogenous elastomeric base membrane is prophylactically impervious.

4. A device according to claim 3, wherein the projections function as levers pivotally connected to each other by the base membrane.

5. A device according to claim 3, wherein the projections are of the same size and extend vertically from opposite sides of the base membrane.

6. A device according to claim 3, wherein the projections extend at an angle from opposite sides of the base membrane.

7. A device according to claim 3, wherein the projections extending from one side of the base membrane are longer than those extending from the opposite side of the base membrane.

8. A device according to claim 1, wherein the projections are substantially conical.

9. A device according to claim 1, wherein said projections are hollow.

10. A device according to claim 9, wherein said projections are substantially frustoconical.

11. A device according to claim 9, wherein each projection has four lobes, the lobes being arranged such that each projection is substantially cruciform in cross section.

12. A device according to claim 11, wherein the projections are arranged in a rectangular array of rows and columns and wherein the lobes of the first projections are adjacent the lobes of the second projections.

13. A device according to claim 9, wherein each projection has a smooth outer surface.

14. A device according to claim 1, wherein the projections are arranged in a rectangular array of rows and columns wherein each row and column the projections on each side of the base are spaced from each other with the projections on one side of the base membrane being offset from the projections on the opposite side of the base.

15. A device according to claim 1, wherein the projections are arranged in a directional array in which the projections on opposite sides of the base membrane are arranged in rows with each projection being adjacent to the next projection, said rows of projections being spaced from each other, the projections in the rows on one side of the base membrane being offset from the projections in the rows on the opposite side of the base membrane.

16. A device for the transmission of information between surfaces comprising a substantially homogenous elastomeric material base membrane having first and second sides and a plurality of first and second hollow, lobed projections spaced apart and integrally formed with said base membrane, the first projections extending from the first side and the second projections extending from the second side 180° from the first projections, the projections being positioned so that an edge of the base of a first projection membrane is in proximity to the opposite edge of the base of a second projection, whereby a force imparting a linear motion to a first projection in a direction parallel to the base membrane results in a similar motion by any cooperating second projections.

* * * * *